(12) United States Patent
Schuessler

(10) Patent No.: US 9,554,724 B2
(45) Date of Patent: Jan. 31, 2017

(54) SELF-ALIGNING SENSOR ARRAY

(71) Applicant: Samsung Electronics, Ltd., Gyeonggi-do (KR)

(72) Inventor: James Schuessler, San Jose, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 539 days.

(21) Appl. No.: 14/103,717

(22) Filed: Dec. 11, 2013

(65) Prior Publication Data

US 2015/0157262 A1    Jun. 11, 2015

(51) Int. Cl.
| A61B 5/00 | (2006.01) |
| A61B 5/053 | (2006.01) |
| A61B 5/026 | (2006.01) |
| A61B 5/024 | (2006.01) |
| A61B 5/0295 | (2006.01) |
| A61B 5/01 | (2006.01) |

(52) U.S. Cl.
CPC .......... *A61B 5/0531* (2013.01); *A61B 5/0261* (2013.01); *A61B 5/0295* (2013.01); *A61B 5/02427* (2013.01); *A61B 5/0533* (2013.01); *A61B 5/681* (2013.01); *A61B 5/01* (2013.01); *A61B 2562/04* (2013.01)

(58) Field of Classification Search
None
See application file for complete search history.

(56) References Cited

U.S. PATENT DOCUMENTS

| 7,618,260 | B2 | 11/2009 | Daniel |
| 8,251,903 | B2 | 8/2012 | LeBoeuf |
| 8,618,930 | B2 | 12/2013 | Papadopoulos |
| 8,647,268 | B2 | 2/2014 | Tran |
| 2009/0306485 | A1 | 12/2009 | Bell |
| 2011/0025493 | A1* | 2/2011 | Papadopoulos .... A61B 5/02427 340/539.12 |
| 2011/0213255 | A1 | 9/2011 | Finburgh |
| 2011/0288382 | A1 | 11/2011 | Finburgh |
| 2012/0065514 | A1* | 3/2012 | Naghavi ............... G06F 19/345 600/454 |
| 2012/0071731 | A1 | 3/2012 | Gottesman |
| 2013/0014706 | A1 | 1/2013 | Menkes |
| 2013/0165817 | A1 | 6/2013 | Horst |
| 2013/0317333 | A1 | 11/2013 | Yang |

(Continued)

OTHER PUBLICATIONS

"Blocks modular smartwatch: Like Project Ara for your wrist," W.Shanklin, Gizmag, Mar. 6, 2014.

(Continued)

*Primary Examiner* — Sath V Perungavoor
*Assistant Examiner* — Dakshesh Parikh
(74) *Attorney, Agent, or Firm* — Convergent Law Group LLP

(57) ABSTRACT

Exemplary embodiments for self-aligning a sensor array with respect to blood vessel of a user comprise: determining an optimal sensor in a sensor array comprising an array of discrete sensors arranged on a band such that the sensor array straddles or otherwise addresses a blood vessel or other targeted area of a user by activating each of the discrete sensors to generate respective signals; designating as the optimal discrete sensor a particular discrete sensor producing a highest signal-to-noise ratio; and using the optimal sensor to collect physiological data of the user.

20 Claims, 3 Drawing Sheets

(56) References Cited

U.S. PATENT DOCUMENTS

2014/0213863 A1* 7/2014 Loseu ................ A61B 5/02416
600/324
2014/0221792 A1* 8/2014 Miller ................ A61B 5/0537
600/309

OTHER PUBLICATIONS

"A Survey on Wearable Sensor-Based Systems for Health Monitoring and Prognosis," A. Pantelopoulos and N.G. Bourbakis, IEEE Transactions on Systems, Man and Cybernetics, vol. 40, No. 1, Jan. 2010.
"Multisensor Fusion in Smartphones for Lifestyle Monitoring," R.K. Ganti, S. Srinivasan, and A. Gacic, International Conference on Body Sensor Networks, 2010.
"A 5.2mW Self-Configured Wearable Body Sensor Network Controller and a 12uW Wireless Powered Sensor for a Continuous Health Monitoring System," J.Yoo, L.Yan, S.Lee, Y.Kim, and H-J Yoo, IEEE Journal of Solid-state Circuits, vol. 45, No. 1, Jan. 2010.

* cited by examiner

Determine an optimal sensor in a sensor array comprising an array of discrete sensors arranged on a band such that the sensor array straddles the blood vessel of a user by activating each of the discrete sensors to generate respective signals
400

Designate as the optimal sensor the discrete sensor producing a highest signal-to noise ratio
402

Use the optimal sensor to collect physiological data from the user
404

FIG. 4

SELF-ALIGNING SENSOR ARRAY

BACKGROUND

Wearable devices are becoming increasingly popular. For example, wearable devices equipped with sensors are known that may capture user data such as activity data (duration, step count, calories burned), sleep statistics, and/or physiological data (e.g., heart rate, perspiration and skin temperature). Typically, sensor-equipped wearable devices are implemented as bands or watches that may be worn on the user's wrist. However, the sensors that record physiological data require precise positional accuracy on the wrist to obtain accurate readings. Consequently, such devices need to be worn tightly fitted to the user's wrist. This may at times oppose the need for the devices to be comfortable to wear for long periods of time. Long term, even continuous use, is important for such devices to obtain data that may offer new or improved insight into one's health.

Accordingly, what is needed is a wearable sensor device that has a sufficiently loose fit to be comfortably worn by the user, while maintaining positional accuracy on the wrist for accurate reading of physiological data.

BRIEF SUMMARY

The exemplary embodiment provides methods and systems for self-aligning a sensor array with respect to a blood vessel or other targeted placement of a sensor on a person's body. Aspects of exemplary environment include determining an optimal sensor in a sensor array comprising an array of discrete sensors arranged on a band such that the sensor array straddles or otherwise addresses a blood vessel of a user by activating each of the discrete sensors to generate respective signals; designating as the optimal discrete sensor a particular discrete sensor producing a highest signal-to-noise ratio; and using the optimal sensor to collect physiological data of the user.

Accordingly, the sensor array is capable of self-aligning to the user's blood vessel to accommodate movement of the band about the body part on which it is worn, while maintaining position accuracy.

BRIEF DESCRIPTION OF SEVERAL VIEWS OF THE DRAWINGS

These and/or other features and utilities of the present general inventive concept will become apparent and more readily appreciated from the following description of the embodiments, taken in conjunction with the accompanying drawings of which:

FIG. 4 is a diagram of a process for self-aligning a sensor array with respect to blood vessel of a user.

DETAILED DESCRIPTION

Figure 1:
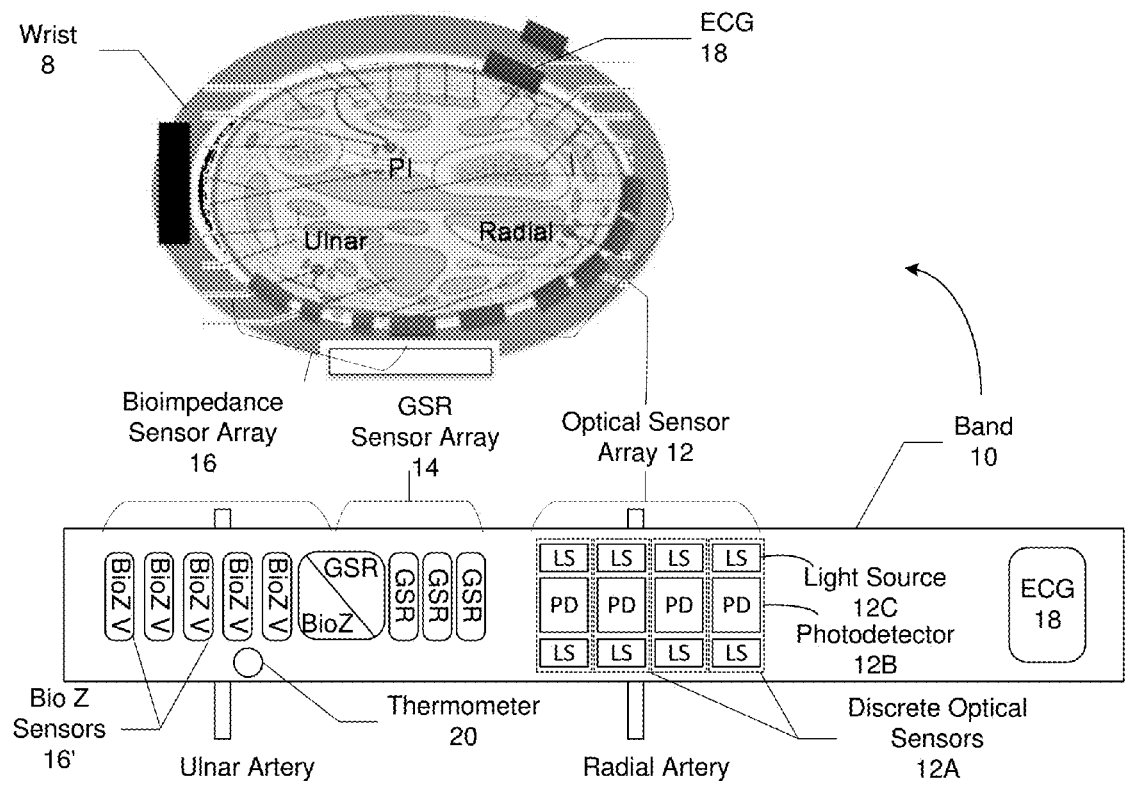
FIG. 1 is a block diagram illustrating an exemplary embodiment of a self-aligning sensor array system.

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Advantages and features of the present invention and methods of accomplishing the same may be understood more readily by reference to the following detailed description of embodiments and the accompanying drawings. The present general inventive concept may, however, be embodied in many different forms and should not be construed as being limited to the embodiments set forth herein. Rather, these embodiments are provided so that this disclosure will be thorough and complete and will fully convey the concept of the general inventive concept to those skilled in the art, and the present general inventive concept will only be defined by the appended claims. In the drawings, the thickness of layers and regions are exaggerated for clarity.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

The term "component" or "module", as used herein, means, but is not limited to, a software or hardware component, such as a field programmable gate array (FPGA) or an application specific integrated circuit (ASIC), which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Exemplary embodiments provide a self-aligning sensor array for use as a wearable device that may be worn relatively loosely, but that also maintains positional accuracy on a user's body part, such a wrist, for accurate reading of physiological data. In one embodiment, the sensor array comprises discrete sensors arranged on a band, such that when worn on a body part of a user, the array of discrete sensors straddles or otherwise addresses a particular blood vessel or other targeted area of the user's body. When the band is worn on a body part such as a wrist or a finger, the band may make contact with the user's skin, but may be loose enough that the band rotates to some degree around the body part. Therefore, an alignment process may be performed to determine which one of the discrete sensors has an optimum position over the blood vessel or other targeted area by activating each of the discrete sensors and designating the discrete sensor that returns the highest signal-to-noise ratio the optimal sensor. The optimal sensor may then be used to collect physiological data from the user. Accordingly, the sensor array is capable of self-aligning to the user's blood vessel to accommodate movement of the band about the body part on which it is worn.

FIG. 1 is a block diagram illustrating an exemplary embodiment of a self-aligning sensor array system. The system includes a band 10 that houses one or more self-aligning sensors arrays. The top portion of FIG. 1 shows the band 10 wrapped around a cross-section of a user's wrist 8, while the bottom portion of FIG. 1 shows the band 10 in an unrolled position.

According to the exemplary embodiment, the band 10 includes at least an optical sensor array 12, and may also include optional sensors, such as a galvanic skin response (GSR) sensor array 14, a bioimpedance (BioZ) sensor array 16, and an electrocardiography sensor (ECG) 18, any combination of which may comprise a self-aligning sensor array.

According to one exemplary embodiment, the self-aligning sensor array(s) comprise an array of discrete sensors that are arranged or laid out on the band 10, such that when the band 10 is worn on a body part, each sensor array straddles or otherwise addresses a particular blood vessel (i.e., a vein, artery, or capillary), or an area with higher electrical response irrespective of the blood vessel. More particularly, the sensor array may be laid out substantially perpendicular to a longitudinal axis of the blood vessel and overlaps a width of the blood vessel to obtain an optimum signal. In one embodiment, the band 10 may be worn so that the self-aligning sensor array(s) on the band 10 contact the user's skin, but not so tightly that the band 10 is prevented from any movement over the body part, such as the user's wrist 8.

In one embodiment, the optical sensor array 12 may comprise a photoplethysmograph (PPG) sensor array that may measures relative blood flow, pulse and/or blood oxygen level. In this embodiment, the optical sensor array 12 may be arranged on the band 10 so that the optical sensor array 12 straddles or otherwise addresses an artery, such as the Radial or Ulnar artery.

The galvanic skin response (GSR) sensor array 14 may comprise four or more GSR sensors that may measure electrical conductance of the skin that varies with moisture level. Conventionally, to GSR sensors are necessary to measure resistance along the skin surface. According to one aspect of the exemplary embodiment, the GSR sensor array 14 is shown including four GSR sensors, where any two of the four may be selected for use. In one embodiment, the GSR sensors 14 may be spaced on the band 2 to 5 mm apart.

The bioimpedance (BioZ) sensor array 16 may comprise four or more BioZ sensors 16' that measure bioelectrical impedance or opposition to a flow of electric current through the tissue. Conventionally, only two sets of electrodes are needed to measure bioimpedance, one set for the "I" current and the other set for the "V" voltage. However, according to an exemplary embodiment, a bioimpedance sensor array 16 may be provided that includes at least four to six bioimpedance sensors 16', where any four of electrodes may be selected for "I" current pair and the "V" voltage pair. The selection could be made using a multiplexor. In the embodiment shown, the bioimpedance sensor array 16 is shown straddling an artery, such as the Radial or Ulnar artery. In one embodiment, the BioZ sensors 16' may be spaced on the band 5 to 13 mm apart. In one embodiment, one or more electrodes comprising the BioZ sensors 16' may be multiplexed with one or more of the GSR sensors 14.

In yet another embodiment, the band 10 may include one or more electrocardiography sensors (ECG) 18 that measure electrical activity of the user's heart over a period of time. In addition, the band may also include a thermometer 20 for measuring temperature or a temperature gradient.

Further details of the optical sensor array 12 will now be discussed. In one embodiment, the optical sensor array 12 may include an array of discrete optical sensors 12A, where each discrete optical sensor 12A is a combination of at least one photodetector 12B and at least two matching light sources 12C located adjacent to the photodetector 12B. In one embodiment, each of the discrete optical sensors 12A may be separated from its neighbor on the band 10 by a predetermined distance of approximately 0.5 to 2 mm.

In one embodiment, the light sources 12C may each comprise light emitting diode (LED), where LEDs in each of the discrete optical sensors 12A emit a light of a different wavelength. Example light colors emitted by the LEDs may include green, red, near infrared, and infrared wavelengths. Each of the photodetectors 12B convert received light energy into an electrical signal. In one embodiment, the signals may comprise reflective photoplethysmograph signals. In another embodiment, the signals may comprise transmittance photoplethysmograph signals. In one embodiment, the photodetectors 12B may comprise phototransistors. In alternative embodiment, the photodetectors 12B may comprise charge-coupled devices (CCD).

Figures 2A, 2B, 2C:
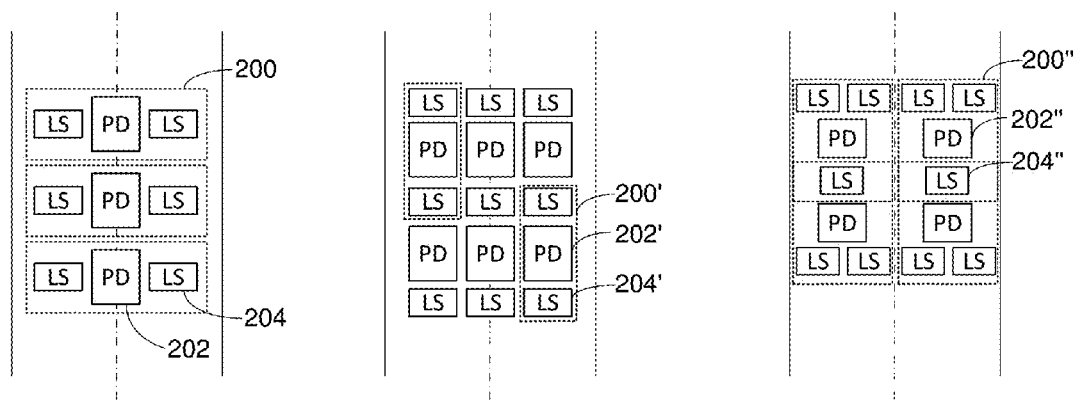
FIGS. 2A-2C are diagrams showing different layout embodiments for the discrete optical sensors.

In one embodiment, configuration and layout of each of the discrete optical sensors 12A may vary greatly depending on use cases. FIGS. 2A-2C are diagrams showing different layout embodiment for the discrete optical sensors. In the embodiments shown in FIGS. 2A-2C the array of discrete optical sensors 200 are arranged along a longitudinal axis of the band 10.

FIG. 2A shows an embodiment where each of the discrete optical sensors 200 is laid out perpendicular to the longitudinal axis of the band, and where each discrete optical sensor 200 comprises a single photodetector 202 centered on the longitudinal axis of the band and two light sources 204 located on each side of the photodetector 200.

FIG. 2B shows an embodiment where each of the discrete optical sensors 200' is laid out parallel to the longitudinal axis of the band and where each discrete optical sensor 200' comprises a single photodetector 202' and a light source 204' located at a top and bottom the photodetector 202'. In a further embodiment, the light sources 204' may be shared between neighboring photodetector 200', as shown.

FIG. 2C shows an embodiment where each of the discrete optical sensors 200" has a triangular configuration comprising a single photodetector 202" surrounded by three light sources 204". In a further embodiment, each photodetector 202 may share one of the light sources 204" with a neighboring photodetector 200", as shown.

In one embodiment, the band 10 may comprise a strip of material that is to be worn on a body part of the user. Examples of the band 10 may include, but are not limited to, a wrist band, an armband, a headband, an ankle bracelet, a choker, and a ring. In an alternative embodiment, the band may also comprise a patch that adheres to the skin of the user.

In one embodiment, the self-aligning sensor array(s) are placed on an inside of the band 10, such that when the band is worn on a body part of the user, the sensor arrays face the skin of the user. According to a further embodiment, the band 10 may include both sensors arrays inside the band 10, and one or more additional sensor arrays on the outside of the band 10 for sensing a body part placed in contact with the outside of the band 10, such as a finger, forehead or leg, for instance.

Figure 3:
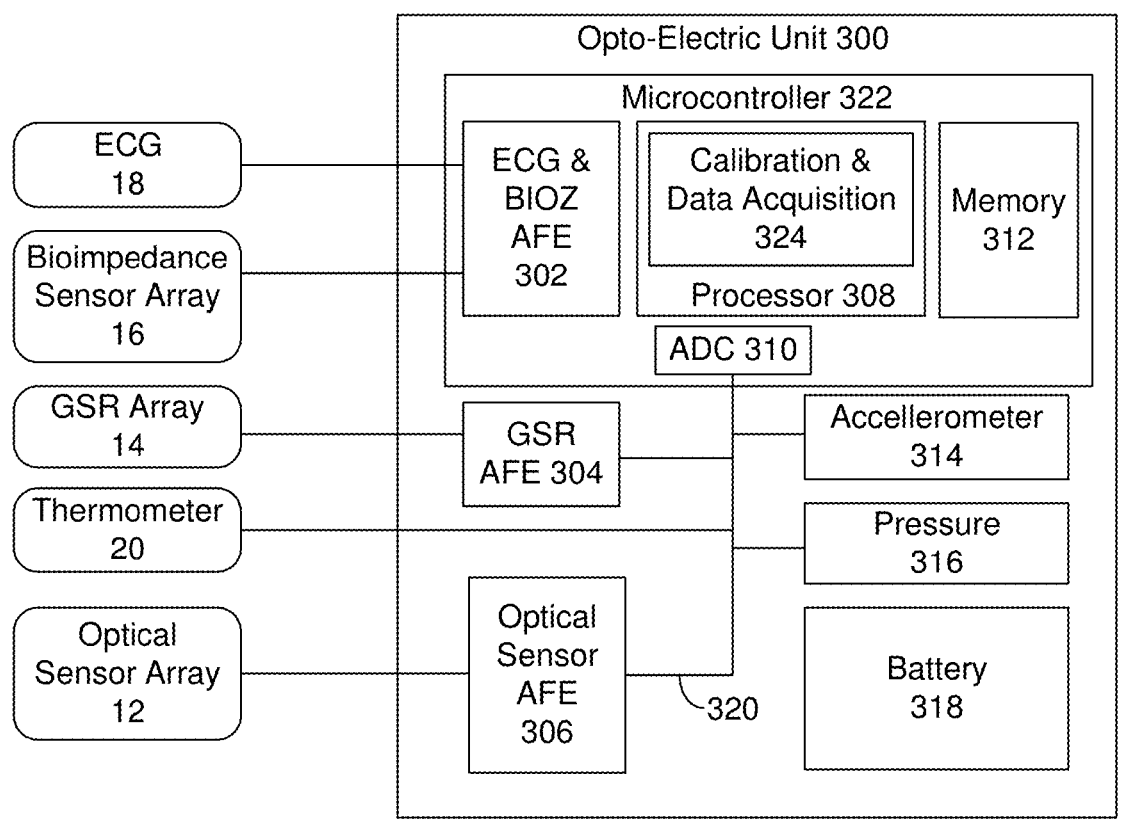
FIG. 3 is a block diagram illustrating components of the self-aligning sensor array system in a further embodiment.

FIG. 3 is a block diagram illustrating components of the self-aligning sensor array system in a further embodiment. In one embodiment, the ECG 18, the bioimpedance sensor array 16, the GSR array 14, the thermometer 20, and the optical sensor array 12 may be coupled to an optical-electric unit 300 that controls and receives data from the sensors on the band 10. In one embodiment, the optical-electric unit 300 may be part of the band 10. In an alternative embodiment, the optical-electric unit 300 may be separate from the band 10.

The optical-electric unit 300 may comprise an ECG and bioimpedance (BIOZ) analog front end (AFE) 302, a GSR AFE 304, an optical sensor AFE 306, a processor 308, and analog-to-digital converter (ADC) 310, a memory 312, an accelerometer 314, a pressure sensor 316 and a battery 318.

As used herein, an AFE may comprise an analog signal conditioning circuitry interface between corresponding sensors and the ADC 310 or the processor 308. The ECG and BIOZ AFE 302 exchange signals with the ECG 18 and the bioimpedance sensor array 16. The GSR AFE 304 may exchange signals with the GSR array 14. And the optical sensor AFE 306 may exchange signals with the optical sensor array 12. In one embodiment, the GSR AFE 304, the optical sensor AFE 306, the accelerometer 314, and the pressure sensor 316 may be coupled to the ADC 310 via bus 320. The ADC 310 may convert a physical quantity, such as voltage, to a digital number representing amplitude.

In one embodiment, the ECG and BIOZ AFE 302, memory 312, the processor 308 and the ADC 310 may comprise components of a microcontroller 322. In one embodiment, the GSR AFE 304 and the optical sensor AFE 306 may also be part of the microcontroller 322. The processor 308 in one embodiment may comprise a reduced instruction set computer (RISC), such as a Cortex 32-bit RISC ARM processor core by ARM Holdings, for example.

According to the exemplary embodiment, the processor 308 may execute a calibration and data acquisition component 324 that may perform sensor calibration and data acquisition functions. In one embodiment, the sensor calibration function may comprise a process for self-aligning one more sensor arrays to a blood vessel. In one embodiment, the sensor calibration may be performed at startup, prior to receiving data from the sensors, or at periodic intervals during operation.

FIG. 4 is a diagram of a process for self-aligning a sensor array with respect to a blood vessel or other targeted area of a user. The process may begin by the calibration and data acquisition component 324 determining an optimal sensor in a sensor array comprising an array of discrete sensors arranged on a band such that the sensor array straddles or otherwise addresses the blood vessel of a user by activating each of the discrete sensors to generate respective signals (block 400). In one embodiment, the optimal sensor refers to a particular discrete sensor having an optimum position over the blood vessel. In one embodiment, the discrete sensors may be activated in series. In an alternative embodiment, the discrete sensors may be activated in parallel.

In the case of the optical sensor array 12, as shown in FIG. 1 for example, the discrete optical sensors 12A may be activated to illuminate tissue of the user with at least two light sources 12C of different wavelength, and the photo detectors 12B measure an amount of light received to generate respective PPG signals.

Referring again to FIG. 4, the calibration and data acquisition component 324 designates as the optimal sensor a particular discrete sensor producing a highest signal-to noise ratio (block 402). That is, the discrete sensor generating the strongest signal may be used to identify the discrete sensor located closest to the blood vessel.

The optimal sensor may then be used to collect physiological data from the user (block 404). Using the optical sensor to collect physiological data from the user may include activating the discrete sensor and receiving the signals output from the discrete sensor for calculation and/or storage.

A method and system for a self-aligning sensor array has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor. Accordingly, many modifications may be made by one of ordinary skill in the art without departing from the spirit and scope of the appended claims.

I claim:

1. A method for self-aligning a sensor array with respect to blood vessel or other targeted area of a user, comprising:
   providing an optical sensor array, the optical sensor array comprising an array of discrete optical sensors arranged on a band, such that the optical sensor array straddles the blood vessel of a user, wherein each of the discrete optical sensors has a triangular configuration comprising a single photodetector surrounded by three light sources that emit light of a different wavelength that is detected by the single photodetector;
   performing, by a processor, a sensor calibration of the optical sensor array at periodic intervals during operation to determine which one of the discrete sensors has an optimum position over the blood vessel, the sensor calibration comprising:
      activating each of the discrete optical sensors to generate respective signals;
      designating as the optimal discrete sensor a particular discrete optical sensor producing a highest signal-to-noise ratio; and
      using the optimal sensor to collect physiological data of the user.

2. The method of claim 1, wherein the optical sensor array is laid out substantially perpendicular to a longitudinal axis of the blood vessel and overlaps a width of the blood vessel.

3. The method of claim 1, wherein activating each of the discrete optical sensors further comprises: illuminating tissue of the user with the light sources and measuring an amount of light received by each of the photodetectors to generate respective signals.

4. The method of claim 1, wherein the respective signals comprise photoplethysmograph (PPG) signals.

5. The method of claim 1, wherein the optical sensor array is arranged on the band so that the optical sensor array straddles a Radial or Ulnar artery.

6. The method of claim 1, wherein the light sources located between neighboring photodetectors are shared by the neighboring photodetectors.

7. The method of claim 1, wherein each of the discrete optical sensors is separated from a neighbor on the band by a predetermined distance of approximately 0.5 to 2 mm.

8. The method of claim 1, wherein the optical sensor array comprises at least one of: a galvanic skin response (GSR) sensor array, and a bioimpedance (BioZ) sensor array.

9. The method of claim 1, wherein a first sensor array is located inside the band and a second sensor array located on an outside of the band.

10. The method of claim 1, wherein the band may comprise one of a wrist band, an armband, a headband, an ankle bracelet, a choker, a ring, and a patch.

11. A self-aligning sensor array, comprising:
an optical sensor array of discrete optical sensors arranged on a band such that the optical sensor array straddles or otherwise addresses a blood vessel of a user, wherein each of the discrete optical sensors has a triangular configuration comprising a single photodetector surrounded by three light sources that emit light of a different wavelength that is detected be the single photodetector;
a processor coupled to the sensor array that performs a sensor calibration of the optical sensor array at periodic intervals during operation to determine which one of the discrete sensors has an optimum position over the blood vessel, the processor configured to:
activate each of the discrete optical sensors to generate respective signals;
designate as the optimal discrete sensor a particular discrete optical sensor producing a highest signal-to-noise ratio; and
use the optimal sensor to collect physiological data of the user.

12. The self-aligning sensor array of claim 11, wherein the optical sensor array is laid out substantially perpendicular to a longitudinal axis of the blood vessel and overlaps a width of the blood vessel.

13. The self-aligning sensor array of claim 11, wherein activating each of the discrete optical further comprises: illuminating tissue of the user with the light sources and measuring an amount of light received by each of the photodetectors to generate respective signals.

14. The self-aligning sensor array of claim 11, wherein the respective signals comprise photoplethysmograph (PPG) signals.

15. The self-aligning sensor array of claim 11, wherein the optical sensor array is arranged on the band so that the optical sensor array straddles a Radial or Ulnar artery.

16. The self-aligning sensor array of claim 11, wherein the light sources located between neighboring photodetectors are shared by the neighboring photodetectors.

17. The self-aligning sensor array of claim 11, wherein each of the discrete optical sensors is separated from a neighbor on the band by a predetermined distance of approximately 0.5 to 2 mm.

18. The self-aligning sensor array of claim 11, wherein the sensor array comprises at least one of: a galvanic skin response (GSR) sensor array, and a bioimpedance (BioZ) sensor array.

19. The self-aligning sensor array of claim 11, wherein a first sensor array is located inside the band and a second sensor array located on an outside of the band.

20. The self-aligning sensor array of claim 11, wherein the band may comprise one of a wrist band, an armband, a headband, an ankle bracelet, a choker, a ring, and a patch.

* * * * *